United States Patent
Moloney et al.

(10) Patent No.: US 12,036,360 B2
(45) Date of Patent: Jul. 16, 2024

(54) CONTROL DEVICE FOR AN ELECTRONIC AEROSOL PROVISION SYSTEM

(71) Applicant: NICOVENTURES TRADING LIMITED, London (GB)

(72) Inventors: Patrick Moloney, London (GB); Anton Korus, London (GB); Justin Han Yang Chan, London (GB)

(73) Assignee: NICOVENTURES TRADING LIMITED, London (GB)

( * ) Notice: Subject to any disclaimer, the term of this patent is extended or adjusted under 35 U.S.C. 154(b) by 801 days.

(21) Appl. No.: 15/733,691

(22) PCT Filed: Mar. 27, 2019

(86) PCT No.: PCT/GB2019/050866
§ 371 (c)(1),
(2) Date: Sep. 29, 2020

(87) PCT Pub. No.: WO2019/186147
PCT Pub. Date: Oct. 3, 2019

(65) Prior Publication Data
US 2021/0015158 A1 Jan. 21, 2021

(30) Foreign Application Priority Data
Mar. 29, 2018 (GB) ........................... 1805169

(51) Int. Cl.
*A61M 15/06* (2006.01)
*A24F 40/48* (2020.01)
(Continued)

(52) U.S. Cl.
CPC ............. *A61M 15/06* (2013.01); *A24F 40/48* (2020.01); *A24F 40/50* (2020.01); *A24F 40/60* (2020.01); *A24F 40/65* (2020.01); *A24F 40/20* (2020.01)

(58) Field of Classification Search
None
See application file for complete search history.

(56) References Cited

U.S. PATENT DOCUMENTS

| 5,144,962 A | 9/1992 | Counts et al. |
| 11,701,479 B1 | 7/2023 | Robinson et al. |

(Continued)

FOREIGN PATENT DOCUMENTS

| AU | 2019244384 B2 | 10/2021 |
| CA | 2827144 A1 | 3/2015 |

(Continued)

OTHER PUBLICATIONS

"Decision of Refusal received for Japanese Patent Application No. 2020-550617, dated Nov. 29, 2022".

(Continued)

*Primary Examiner* — Tho D Ta
(74) *Attorney, Agent, or Firm* — BURR & FORMAN LLP

(57) ABSTRACT

A control device for an electronic aerosol provision system is configured to receive a replaceable component to form an electronic aerosol provision system. The control device is further configured to receive an identifier from a replaceable component received by the control device; and to modify one or more characteristics (such as resistance to draw, RTD) of an airflow path through the electronic aerosol provision system dependent upon the received identifier.

19 Claims, 5 Drawing Sheets

(51) Int. Cl.
- *A24F 40/50* (2020.01)
- *A24F 40/60* (2020.01)
- *A24F 40/65* (2020.01)
- *A24F 40/20* (2020.01)

(56) References Cited

U.S. PATENT DOCUMENTS

| | | |
|---|---|---|
| 2007/0074722 A1 | 4/2007 | Giroux et al. |
| 2008/0110452 A1 | 5/2008 | Kotnik et al. |
| 2009/0043613 A1 | 2/2009 | Jung et al. |
| 2009/0090363 A1 | 4/2009 | Niland et al. |
| 2009/0294521 A1 | 12/2009 | De |
| 2013/0042865 A1 | 2/2013 | Monsees et al. |
| 2013/0284192 A1 | 10/2013 | Peleg et al. |
| 2014/0096781 A1 | 4/2014 | Sears et al. |
| 2014/0261492 A1 | 9/2014 | Kane et al. |
| 2014/0334804 A1 | 11/2014 | Choi |
| 2015/0027457 A1 | 1/2015 | Janardhan et al. |
| 2015/0105701 A1 | 4/2015 | Mayer et al. |
| 2015/0245662 A1 | 9/2015 | Memari et al. |
| 2015/0258289 A1* | 9/2015 | Henry, Jr. .............. A24F 40/50 128/202.21 |
| 2016/0338407 A1 | 11/2016 | Kerdemelidis |
| 2016/0346489 A1 | 12/2016 | Finke et al. |
| 2017/0000192 A1* | 1/2017 | Li ........................ G05B 15/02 |
| 2017/0020191 A1 | 1/2017 | Lamb et al. |
| 2017/0042214 A1* | 2/2017 | Murison ................. G06F 21/44 |
| 2017/0048927 A1* | 2/2017 | Murison ................. H02J 7/342 |
| 2017/0224014 A1 | 8/2017 | Fraser et al. |
| 2017/0231277 A1 | 8/2017 | Mironov et al. |
| 2017/0258136 A1 | 9/2017 | Hawes et al. |
| 2017/0280774 A1* | 10/2017 | Force ...................... A24F 40/42 |
| 2018/0020733 A1 | 1/2018 | Jochnowitz |
| 2019/0000144 A1 | 1/2019 | Bless et al. |
| 2019/0387796 A1 | 12/2019 | Cohen |
| 2020/0000143 A1 | 1/2020 | Anderson et al. |
| 2020/0338282 A1 | 10/2020 | Trzecieski |
| 2021/0134095 A1 | 5/2021 | Milt et al. |
| 2021/0251044 A1 | 8/2021 | Reevell |
| 2021/0378312 A1 | 12/2021 | Talbot et al. |
| 2022/0061399 A1 | 3/2022 | Ferrie et al. |
| 2022/0202079 A1 | 6/2022 | Mcguinness et al. |
| 2022/0225684 A1 | 7/2022 | Pueschner et al. |
| 2023/0200454 A1 | 6/2023 | Li et al. |

FOREIGN PATENT DOCUMENTS

| | | | | |
|---|---|---|---|---|
| CA | 2940693 A1 | 9/2015 | | |
| CN | 1356783 A | 7/2002 | | |
| CN | 201630238 | 11/2010 | | |
| CN | 102264251 A | 11/2011 | | |
| CN | 103914013 A | 7/2014 | | |
| CN | 103997921 A | 8/2014 | | |
| CN | 104303524 A | 1/2015 | | |
| CN | 105792687 A | 7/2016 | | |
| CN | 106136330 A | 11/2016 | | |
| CN | 106170215 A | 11/2016 | | |
| CN | 106455717 A | 2/2017 | | |
| CN | 106666834 A | 5/2017 | | |
| CN | 106998818 A * | 8/2017 | .......... | A24B 15/167 |
| CN | 107533582 A | 1/2018 | | |
| EP | 0691083 A1 | 1/1996 | | |
| EP | 2201850 A1 * | 6/2010 | .............. | A24D 1/20 |
| EP | 3216357 A1 | 9/2017 | | |
| GB | 2542270 A | 3/2017 | | |
| JP | H03290279 A | 12/1991 | | |
| JP | 2005198538 A | 7/2005 | | |
| JP | 2012513750 A | 6/2012 | | |
| JP | 2015507477 | 3/2015 | | |
| JP | 2017510270 A | 4/2017 | | |
| JP | 2017513465 A | 6/2017 | | |
| JP | 2017522876 A | 8/2017 | | |
| JP | 2017531337 A | 10/2017 | | |
| JP | 2020532973 | 11/2020 | | |
| KR | 20170121162 A | 11/2017 | | |
| RU | 2061396 | 6/1996 | | |
| RU | 2085092 C1 | 7/1997 | | |
| RU | 2517125 C2 | 5/2014 | | |
| RU | 2645324 C2 | 2/2018 | | |
| RU | 2647805 C2 | 3/2018 | | |
| TW | 201735805 A | 10/2017 | | |
| WO | 2009112182 A1 | 9/2009 | | |
| WO | 2011160788 A1 | 12/2011 | | |
| WO | 2014150247 A1 | 9/2014 | | |
| WO | 2015073854 A2 | 5/2015 | | |
| WO | 2015082560 A1 | 6/2015 | | |
| WO | WO-2015107552 A1 * | 7/2015 | .......... | A24F 47/008 |
| WO | 2016019353 A1 | 2/2016 | | |
| WO | 2016091658 A1 | 6/2016 | | |
| WO | 2016143079 | 9/2016 | | |
| WO | WO-2016135271 A1 * | 9/2016 | ............. | A24F 40/46 |
| WO | 2016187695 A1 | 12/2016 | | |
| WO | 2016199066 A1 | 12/2016 | | |
| WO | 2017011419 A1 | 1/2017 | | |
| WO | 2017019428 A1 | 2/2017 | | |
| WO | 2017029089 A1 | 2/2017 | | |
| WO | WO-2017055801 A1 * | 4/2017 | ............. | A24F 40/50 |
| WO | WO-2017205692 A1 * | 11/2017 | ............. | A24F 40/10 |
| WO | 2017207442 | 12/2017 | | |
| WO | 2018020599 A1 | 2/2018 | | |
| WO | 2018020619 A1 | 2/2018 | | |
| WO | 2019048211 | 3/2019 | | |

OTHER PUBLICATIONS

"Decision to Grant a Patent received for Japanese Patent Application No. 2020-548975, dated May 24, 2022".

"International Preliminary Report on Patentability received for PCT Patent Application No. PCT/GB2019/050866, dated Sep. 22, 2020".

"International Preliminary Report on Patentability received for PCT Patent Application No. PCT/GB2019/050867, dated Oct. 8, 2020".

"International Preliminary Report on Patentability received for PCT Patent Application No. PCT/GB2019/050868, dated Oct. 8, 2020".

"International Search Report and Written Opinion received for PCT Patent Application No. PCT/GB2019/050866, dated Sep. 17, 2019".

"International Search Report and Written Opinion received for PCT Patent Application No. PCT/GB2019/050867, dated Jun. 6, 2019".

"International Search Report and Written Opinion received for PCT Patent Application No. PCT/GB2019/050868, dated Jun. 6, 2019".

"Invitation to Pay Additional Fees received for PCT Patent Application No. PCT/GB2019/050866, dated Jul. 22, 2019".

"Notice of Allowance received for Chinese Patent Application No. 201980022789.1, dated Jul. 28, 2023".

"Notice of Allowance received for Russian Patent Application No. 2021133410, dated Jul. 10, 2023".

"Notice of Reason for Rejection received for Japanese Application No. 2020-549008, dated Sep. 21, 2021".

"Notice of Reasons for Refusal received for Japanese Patent Application No. 2020-550617, dated Nov. 16, 2021".

"Office Action and Search Report received for Chinese Application No. 2019800216825, dated Dec. 23, 2022".

"Office Action and Search Report received for Chinese Patent Application No. 201980023364.2, dated Dec. 27, 2022".

"Office Action received for Chinese Patent Application No. 201980021682.5, dated Jul. 15, 2023".

"Office Action received for Chinese Patent Application No. 2019800227891, dated Jan. 20, 2023".

"Office Action received for Korean Patent Application No. 10-2020-7027669, dated Jan. 18, 2023".

"Office Action received for Korean Patent Application No. 10-2020-7027669, dated Jul. 7, 2022".

"Office Action received for Korean Patent Application No. 1020207028089, dated Jan. 20, 2023".

"Office Action received for Korean Patent Application No. 10-2020-7028191, dated Jan. 30, 2023".

"Office Action received for Russian Patent Application No. 2020131877, dated Apr. 28, 2021".

"Search Report received for Great Britain Application No. 1805170.6, dated Sep. 20, 2018".

(56) References Cited

OTHER PUBLICATIONS

"Search Report received for Russian Patent Application No. 2020131746, dated Jun. 10, 2021".
"Search Report received for Russian Patent Application No. 2020131821, dated Jun. 21, 2021".
Zhang, et al., "Food Nutrition and Hygiene", China Business Press, May 31, 1989, p. 143.

* cited by examiner

CONTROL DEVICE FOR AN ELECTRONIC AEROSOL PROVISION SYSTEM

PRIORITY CLAIM

The present application is a National Phase entry of PCT Application No. PCT/GB2019/050866, filed Mar. 27, 2019, which claims priority from GB Patent Application No. 1805169.8, filed Mar. 29, 2018, each of which is hereby fully incorporated herein by reference.

FIELD

The present disclosure relates to an electronic aerosol provision system, which may also be referred to (for example) as an e-cigarette, vaping device, electronic vapor provision system (or device), and other similar terms.

BACKGROUND

Many e-cigarettes include a reservoir of liquid (often synthetic) which is vaporized for inhalation. The liquid is more generally referred to as an aerosol precursor material. The reservoir of liquid may be provided in a replaceable component, frequently called a cartridge or cartomizer, which can be attached to, and detached from, the remainder of the e-cigarette.

Other e-cigarettes, sometimes referred to as tobacco heated products (THPs), may include an aerosol precursor (consumable) material derived from tobacco (or potentially from other plants). This aerosol precursor material is heated to produce a vapor for inhalation. Heating the THP consumable does not involve burning the THP consumable, i.e. pyrolysis, as for a conventional cigarette. The THP aerosol precursor material is typically in non-liquid form, e.g. dried leaves, solid powder, reconstituted plant material, gel, etc. In many cases, the THP consumable may include an outer container (such as one or more paper layers) within which an aerosol precursor material is provided. The THP consumable may be used only once, i.e. for one smoking session, analogous to a single (conventional) cigarette. This is in contrast to e-cigarettes having a liquid consumable, for which a cartridge may last for multiple smoking sessions, sometimes for multiple days. The rapid turnover of THP consumable containers means there is considerable interest in making them as simple and cost-effective as possible.

More generally, many electronic aerosol provision systems include a reusable component, often containing a control system and a re-chargeable battery, for use with a replaceable (disposable) component, often containing an aerosol precursor material (whether solid or liquid) that is used as a precursor for generating a vapor or aerosol for inhalation. During the lifetime of such an electronic aerosol provision system, the reusable component (also referred to as a control unit) may be utilized in conjunction with a number of different replaceable components (also referred to as consumables or cartridges). For example, a user may replace the replaceable component if its aerosol precursor material has been exhausted, or if the user would prefer to use a different replaceable component, such as one having an aerosol precursor material for providing another flavor. Accordingly, it is desirable to be able to maintain good compatibility between a control unit and different replaceable components or cartridges that might be attached to (received by) the control unit.

SUMMARY

As described herein, a control device for an electronic aerosol provision system is configured to receive a replaceable component to form an electronic aerosol provision system. The control device is further configured to receive an identifier from a replaceable component received by the control device; and to modify one or more characteristics (such as resistance to draw, RTD) of an airflow path through the electronic aerosol provision system dependent upon the received identifier.

As described herein, a control device for an electronic aerosol provision system is configured to receive a replaceable component to form an electronic aerosol provision system. The control device is further configured to: receive an identifier from a replaceable component received by the control device; and to provide output to a user based on the received identifier, for example, by using a display of the electronic aerosol provision system.

Also provided is a method of operating a control device for an electronic aerosol provision system. The method comprises receiving a replaceable component to form an electronic aerosol provision system, and receiving an identifier from the replaceable component. The method further comprises, in response to the received identifier, performing at least one of: modifying the resistance to draw of an airflow path through the electronic aerosol provision system dependent upon the received identifier; and/or providing output to a user based on the received identifier, such as by using a display of the electronic aerosol provision system.

As described herein, a control device for an electronic aerosol provision system is configured to receive a replaceable component to form an electronic aerosol provision system. The control device is further configured to use electric power from a battery within the electronic aerosol provision system to modify the resistance to draw through the electronic aerosol provision system, such as by constricting the airflow path.

It will be appreciated that features and aspects of the disclosure described above in relation to the first and other aspects of the disclosure are equally applicable to, and may be combined with, embodiments of the disclosure according to other aspects of the disclosure as appropriate, and not just in the specific combinations described above.

BRIEF DESCRIPTION OF THE DRAWINGS

Various implementations of the disclosure will now be described, by way of example only, with reference to the accompanying drawings, in which.

DETAILED DESCRIPTION

The present disclosure relates to an aerosol provision device, also referred to as an aerosol provision system, an e-cigarette, a vapor provision system and similar. In the following description, the terms "e-cigarette" and "electronic cigarette" are generally used interchangeably with (electronic) vapor provision system/device, unless otherwise clear from the context. Likewise, the terms "vapor" and "aerosol", and related terms such as "vaporize", "volatilize" and "aerosolize", are generally used interchangeably, unless otherwise clear from the context.

Aerosol provision systems often have a modular design including, for example, a reusable module (a control or device unit) and a replaceable (disposable) cartridge module containing a liquid aerosol precursor material. The replaceable cartridge typically comprises the aerosol precursor and a vaporizer, such as a heater (and hence is sometimes referred to as a cartomizer), while the reusable module typically comprises the power supply, for example a rechargeable battery, and control circuitry. In some systems, the aerosol precursor may be a liquid, such as a synthetic e-liquid, contained in a reservoir within the cartridge module, which is then vaporized by heating. In some systems, the aerosol precursor material may be in a non-liquid form, such as dried leaves, solid powder, or gel, which are derived, for example, from tobacco plants. Such an aerosol precursor material may then be heated to release vapor. Some systems, which may be referred to as hybrids, may make use of both an e-liquid and a non-liquid aerosol precursor material. For example, in such a system the e-liquid may be vaporized by heating, and the resulting vapor passed through the non-liquid aerosol precursor to generate additional vapor and/or capture flavor from the latter.

It will be appreciated the reusable and disposable modules may include further elements depending on functionality. For example, the control unit may comprise a user interface for receiving user input and displaying operating status characteristics, and/or the replaceable cartridge part may include a temperature sensor for use in helping to control temperature.

In operation, a cartridge is typically electrically and mechanically coupled (in removable fashion) to a control unit using (for example) a screw thread, latching or bayonet fixing with appropriately engaging electrical contacts. When the vapor precursor in the cartridge is exhausted, or the user wishes to switch to a different cartridge (perhaps having a different vapor precursor or flavor), the cartridge may be removed (detached) from the control unit and a replacement cartridge attached in its place. Devices conforming to such a two-part modular configuration may be referred to as a two-part device, although the approach described herein can also be applied if appropriate to devices having more than two components or modules.

Figure 1:
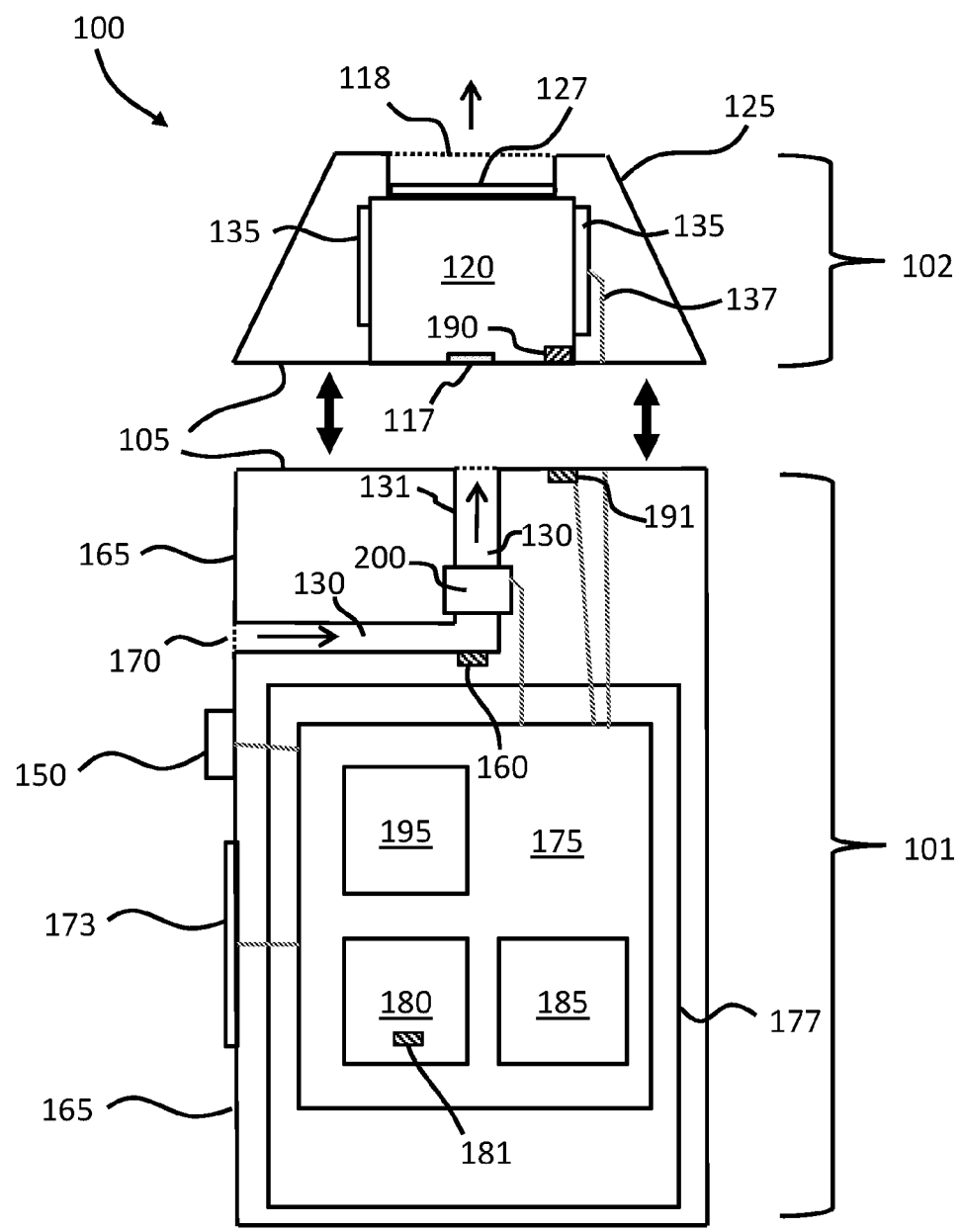
FIG. 1 is a schematic cross-section of an electronic aerosol provision device according to various implementations of the disclosure.

FIG. 1 is a schematic cross-sectional view through an example aerosol provision device 100. The aerosol provision device 100 comprises two main components or modules, namely a reusable/control unit 101 and a replaceable/disposable cartridge 102. In normal use the reusable part 101 and the cartridge 102 are releasably coupled together at an interface 105 (a connection interface) as shown by the two bi-directional arrows. The interface 105 generally provides a structural, electrical and air path connection between the two parts 101, 102 and may utilize a latch mechanism, bayonet fixing or any other form of mechanical coupling as appropriate. The interface 105 typically also provides an electrical coupling between the two parts, which may be wired using connectors, or may be wireless, for example, based on induction.

In FIG. 1, the cartridge 102 comprises a chamber or container 120 for holding an aerosol precursor material; in one example described herein, this material is a solid or non-liquid material such as dried leaves, solid powder, gel, etc. which provides an aerosol (for user inhalation) via the application of heat. In particular, the material container 120 is formed within an outer shell or housing 125. In the example, the outer shell 125 is further structured as a mouthpiece to provide an air outlet 118. In other examples the mouthpiece may be a separate component with the outer shell 125 configured to attach between the reusable part 101 and the mouthpiece.

The housing 125 and the mouthpiece may be provided as one integral component, formed directly as a single unit at manufacture, or may be formed from two parts which are then assembled together at manufacture in a substantially permanent fashion. For example, the housing 125 and mouthpiece may be fixed to each other along a join by friction welding, spin welding, ultrasonic welding, and so on (or by any other suitable technique). The cartridge housing 125 may be formed of plastic. It will be appreciated that the specific geometry of the housing 125, along with the materials, sizing, etc, may vary according to the particular design of a given implementation.

In some examples, when the cartridge 102 is exhausted or the user wishes to switch to a different cartridge, the cartridge 102 may be removed from the reusable part 101 and a new cartridge 102 attached to the reusable part 101 in its place. In the same or other examples, a user may be able to remove the solid material container 120 from the housing 125, for example, in order to provide a new solid material container 120 that includes fresh tobacco or other material. In this way the same cartridge may be reused if necessary. It will be appreciated that such a cartridge 102 will generally have a chamber or similar configured to receive the container 120.

The cartridge 102 has a heater 135 for heating the material contained in the material container 120. The heater 135 may be, for example, an electrically resistive heater, a ceramic heater, and so on. The heater 135 may form one or more walls or boundaries of the material container 120. The heater 135 is configured to provide heat to the material in material container 120 such that it is heated sufficiently to produce an aerosol for inhalation, but not to such a high temperature that the material in material container 120 combusts.

In use, the cartridge 102 is attached to reusable part 101 to allow the heater 135 to receive power by wires connected across interface 105 to the reusable part 101. Interface 105 is provided with electrical contacts or connectors, not shown in FIG. 1, to link wires 137 in the cartridge 102 with corresponding wires in the reusable part 101 (more generally, the wiring of FIG. 1 is shown only in schematic form, rather than indicating the detailed path and nature of such wiring). Some devices allow the heating power to be varied using a suitable control interface that alters the amount of power supplied to the heater 135 during activation. The adjustment in power level supplied from the reusable part to the heater 135 may be implemented using pulse width modulation or any other suitable control technique. The device 100 may be activated by the user inhaling on mouthpiece 118, which triggers a puff detector or airflow sensor 160 to detect the airflow or change in pressure resulting from the inhalation. Other types of device may be activated additionally or alternatively by a user pressing a button 150 or similar on the outside of the device.

In response to a puff (inhalation) or button press being detected, the reusable part 101 provides electrical power to activate the heater 135 to create an aerosol. The aerosol thereby formed is drawn by user inhalation from the container 120, before exiting through mouthpiece 118 for inhalation by the user.

The solid material container 120 is linked to an airflow channel 130 by a first end wall 117 and (at the mouth end) by a second end wall 127. Each end wall 117, 127 is designed to retain the solid material in container 120 while allowing the passage of airflow along channel 130, through the container 120, and out through mouthpiece 118. This may be achieved for example by the end walls 117, 127 having suitably fine holes that retain the granules (or the like) of the solid material in container 120, but allow air to flow through the holes. The end walls 117, 127 of the material container 120 may be provided by separate retainers, for example in the form of disks which are inserted into each end of the housing 125 during manufacture. As an alternative, one or both of the end walls 117, 127 may be formed directly as part of the material container 120.

The reusable part 101 comprises a housing 165 with an opening that defines one or more air inlets 170 for the e-cigarette, a battery 177 for providing operating power to the device, control circuitry 175, a user input button 150, a visual display 173, and puff detector 160. In the configuration shown in FIG. 1, the battery 177 and the control circuitry 175 have a generally planar geometry, with the battery 177 underlying the control circuitry. The housing 165 may be formed, for example, from a plastics or metallic material and has a cross-section generally conforming to the shape and size of the cartridge part 102, so as to provide a smooth outer surface at the transition between the two parts at the interface 105. The battery 177 is rechargeable and may be recharged through a USB connector (not shown in FIG. 1) in the reusable part housing 165.

In the device 100 shown in FIG. 1, air pathway 130 starts at air inlet 170 of reusable part 101 and connects to the material container 120 through the interface 105. Air pathway or channel 130 is defined by sidewall(s) 131 which may for example, may form a channel having a circular cross-sectional profile with a fixed diameter or a variable diameter with respect to the length of the channel. In other examples the cross-sectional profile of channel 130 may have a rectangular or hexagonal cross section, for example, or any other suitable shape. Furthermore the cross-sectional profile of channel 130 may change between different portions of its length. Situated along the air pathway 130 is an airflow modifier 200 operable to modify (i.e. alter, change, or adjust etc.) the resistance to draw through the e-cigarette during a user inhalation, as described in more detail below The puff detector (sensor) 160 is positioned within or adjacent to the airflow pathway 130 of the reusable part 101 to inform the control circuitry 175 when a user inhales on the device 100. The combination of the air inlet 170, airflow channel 130, material container 120 and mouthpiece 118 can be considered to form or represent the primary airflow path of the e-cigarette 100, whereby the airflow resulting from a user inhalation travels in the direction indicated by the single-headed arrows in FIG. 1, from air inlet 170 (upstream) to the mouthpiece 118 (downstream).

The user input button 150 may be implemented in any suitable fashion, e.g. as a mechanical button, a touch-sensitive button etc., and allows various forms of input by the user. For example, the user might use the input button 150 to switch the device off and on (whereby puff detection to activate the heater is only available when the device is switched on). The user input button 150 may also be used to perform control settings, such as adjusting the power level. The display 173 provides a user with a visual indication of various characteristics associated with the electronic cigarette, for example the current power level setting, remaining battery power, on/off status and so forth. The display may be implemented in various ways, for example, using one or more light emitting diodes (LEDS) (potentially multi-colored) and/or as a small liquid crystal display (LCD) screen. Some e-cigarettes may also provide other forms of information to a user, for example using audio signaling and/or haptic feedback.

The control circuitry (alternatively controller or control unit) 175 may be provided by a printed circuit board (PCB) and/or other electronics or circuitry for generally controlling the aerosol provision device. The control circuitry 175 includes a processor 185 or microcontroller (or similar), which is programmed or otherwise configured to control the operations of the aerosol provision device 100, a non-volatile memory 180 for storing programming and/or configuration settings, and a communications interface 195 for communicating with systems and devices external to the device 100. The memory may include a set of stored identifiers 181 and other associated information as described later in more detail.

In operation, the control circuitry 175 may be notified of a puff detection from puff detector 160 and/or a press of button 150, and be configured to respond to such notification to supply electrical power from the battery 177 to the heater/vaporizer 135 through wires 137 to generate vapor for user inhalation. The control circuitry 175 can also monitor additional states within the device, such as the battery power level, and provide a corresponding output via display 173.

In some implementations, the characteristics of the aerosol substrate material in container 120, such as the flavor or nicotine strength, may vary, for example, with different batches or origins for different cartridges. As such, it may be useful for the identity of the material within container 120 to be made available to the control circuitry 175, which may store in memory 180 actions (programming) associated with different types of cartridge. For example, the programming may enable the control circuitry 175 to provide appropriate control signals and power levels for appropriate operation of the heater 135 for the given type of material within container 120. By way of example, the (flavor) compositions used in different aerosol precursor materials may deliver flavor at different rates or at different operating temperatures and, in order to ensure a consistent or an appropriate flavor delivery, control signals may be provided to provide suitable operation of the heater 135. In some cases, the programming may allow the selection of an appropriate heating profile in response to the identification of container 120, thereby enabling the material within the container 120 to be heated in a desired manner to ensure a particular user experience (and to help prevent undesirable effects such as burning of the material).

Different variants or types of container 120 may be offered by a single manufacturer or by multiple difference manufacturers. As a result, there may be a large selection of different containers 120 having a range of attributes, features and so on available for use in the electronic aerosol provision system 100. As described herein, each container may have an identifier component 190 which may be recognized or otherwise interpreted by an identifying component 191 of the connection interface 105, thereby allowing the control unit 101 to determine (for example) the type and/or variant of the container 120 of cartridge 101 (and the material within).

As an example the identifier component 190 may be an optically distinguishable pattern (such as a barcode) and the identifying component 191 may be an optical reader (such as a barcode scanner). In some cases, the bar code or other identifier may be arranged in a longitudinal direction, such that the optical reader scans along the bar code as the cartridge 101 is received into the control unit 102. In other implementations, the identifier component 190 may comprise a suitable electrical memory, such as ROM, a gate array, etc. In such implementations, the identifying component 191 may be implemented with the processor 185 (for example) to access an identifier from the electrical memory when the cartridge is coupled to (engaged with) the control unit 102. In other implementations, the identifier component 190 may comprise an RFID tag or similar, which is then read by the identifying component 191 when the cartridge is received into (or possibly just brought near) the control unit 102. It will be appreciated that there are many other methods which could be used by the identifier component 190 and the identifying component 191 to pass an identifier from the cartridge to the control unit.

A set of identifiers 181 may be stored in the memory 180 of the control circuitry 175, the identifiers typically relating different variants of the container 120 or cartridge. The set may include any number of identifiers; e.g., one identifier, or two or more identifiers. In some examples, each variant (i.e., each variant of aerosol precursor material, and/or of each container 120) may be assigned a specific identifier. In other examples, several variants may be grouped together and assigned the same identifier, for example if they share similar characteristics. By way of example, if two different flavors compositions release flavor at the same rate and/or at the same operating temperature, they may be assigned the same identifier.

The memory 180 may also be used to store actions or programming associated with each identifier. Such programming may be to select a certain heating profile for a given variant of cartridge (for example). There may be a one-to-one relationship between an identifier stored in memory 180 and the various heating profiles, or different groups of identifiers may correspond to different heating profiles. The control actions may also be used to determine different settings for the airflow modifier 200, as described in more detail below.

In some implementations, the control circuitry 175 may process the identifier 190 prior to enabling heater 135 operation. For example, the control circuitry 175 may not supply power to operate the heater if container 120 (and the material within) are not suitable for use with that heater—such as because the heater is not powerful enough to vaporize the material within container 120. Operation may also be prevented if the identifying component 191 does not recognize the identifier received from the cartridge 102—this might indicate, for example, that the cartridge is a counterfeit or unlicensed product, and hence may not be properly compatible with the control unit 101. Accordingly, the set of stored identifiers may be controlled, for example, to ensure that only suitably authorized containers 120 or cartridges 102 are used with the control unit 101.

Accordingly, the present approach utilizes control circuitry 175 which is configured to identify the material container 120 and/or the cartridge section 102 attached for use with control unit 101. One or more characteristics of the cartridge may be deduced from the identifier received from the cartridge, and this information is then used by the control unit during subsequent use of the electronic aerosol provision system.

The set of stored identifiers in the control unit memory 180 may be updated, for example, when a new variant (of the cartridge 102 or container 120) is introduced, e.g. having a different aerosol precursor material. One or more new identifiers for the new cartridge can be added to the set of authorized identifiers held in memory 180. Similarly, identifiers held in memory 180 may be removed or rendered obsolete when a variant is no longer sold. Furthermore, other updates may be performed, such as to alter the association of a particular identifier held in memory 180 with a variant, or to modify the actions stored or associated with the set of stored identifiers. For example, when a new identifier is added to the set of stored identifiers, corresponding actions (such as a new heating profile) may also be added. Additionally, in some cases the actions associated with an identifier may be modified without changing the identifier or its association with a particular variant. This updating of the set of stored identifiers 181 and/or their corresponding actions is facilitated by the communications interface 195 of the control circuitry 175. In some examples, the communications interface 195 may be a transceiver operable to communicate wirelessly with systems and devices external to the aerosol provision device 100. In some cases, an external system or device may act as an intermediary to support indirect communication between the aerosol provision device 100 and one or more remote servers etc.

FIG. 2 shows a flowchart of an example method of operating an electronic aerosol provision system 100 such as shown in FIG. 1 (or the control unit 101 thereof), the device having a memory 180 holding a set of stored identifiers 181. In 310, the control unit 101 receives control information from a remote server via the communication interface 195. According to the particular implementation, the communication interface 195 may support wired and/or wireless communications with an external device (i.e. external to the electronic aerosol provision system). The external device or system may either contain the control information (and so act itself as a remote server), or may facilitate access to a remote server storing the control information. For example, the external device or system might be a smartphone or a laptop or other local device that links over the Internet to the remove server. The received control information may comprise instructions to be performed (for example by the processor 185) and/or data, such as one or more identifiers. The instructions and the data may be saved into memory 180 (or any other appropriate storage device or component).

In 320, the control unit updates the set of stored identifiers based on the control information received from the remote server. Updates to the set of stored identifiers may include adding a new identifier to the set of stored identifiers, removing an identifier from the set of stored identifiers, and/or modifying an identifier of the set of stored identifiers, as appropriate.

In some cases, the control information may comprise a complete set of (updated) information relating to the stored identifiers. In this case, one option is for the control unit to overwrite all the control information previously stored in memory 180 with the newly received information. In other cases, the control unit may compare the newly received control information with the control information already held in memory, and only perform updates in respect of changed information (i.e. additions, deletions and/or modifications). In other cases, the control information may itself be formatted as a set of update actions (add this, delete, this and modify this).

In 330, the control unit updates control actions held in memory that relate (correspond) to various stored identifiers, based on the control information received from the remote server at operation 310. For example, each stored identifier may have its own respective control action, or a subset of stored identifiers may share a respective set of one or more control actions. As with the identifier updates, the format of the control action updates may vary according to the implementation—e.g. a complete overwrite of the previously stored control actions, or just selective updating.

In 340, the control unit updates associations between the identifiers in the set of stored identifiers and the control actions, based on the control information received from the remote server. For example, one of the stored identifiers may be associated with a newly provided (updated) control action, or an association may be updated to link a stored identifier with a different (but already stored) action. Furthermore, if a subset of stored identifiers is associated with a particular control action, the control information may update the identifiers within that subset, for example identifiers may be added or removed.

It will be appreciated that as for the identifier updates, the format of the control action updates and/or the association updates may vary according to the implementation—e.g. a complete overwrite of the previously stored control actions and/or associations may be performed, or just selective updating. In addition, some updates of received control information may not contain updates for stored identifiers, control actions and associations, but rather may contain updates for any one or two of these categories.

Figure 2:
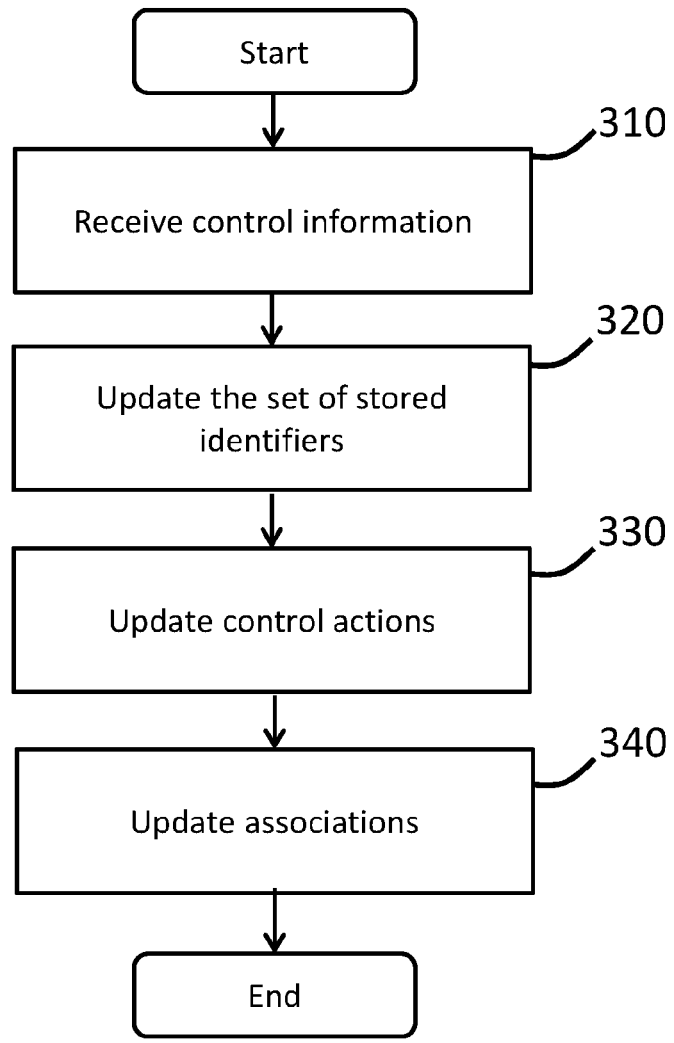
FIG. 2 is a schematic flow diagram of a method to be performed by a control unit according to various implementations of the disclosure.
Figure 3:
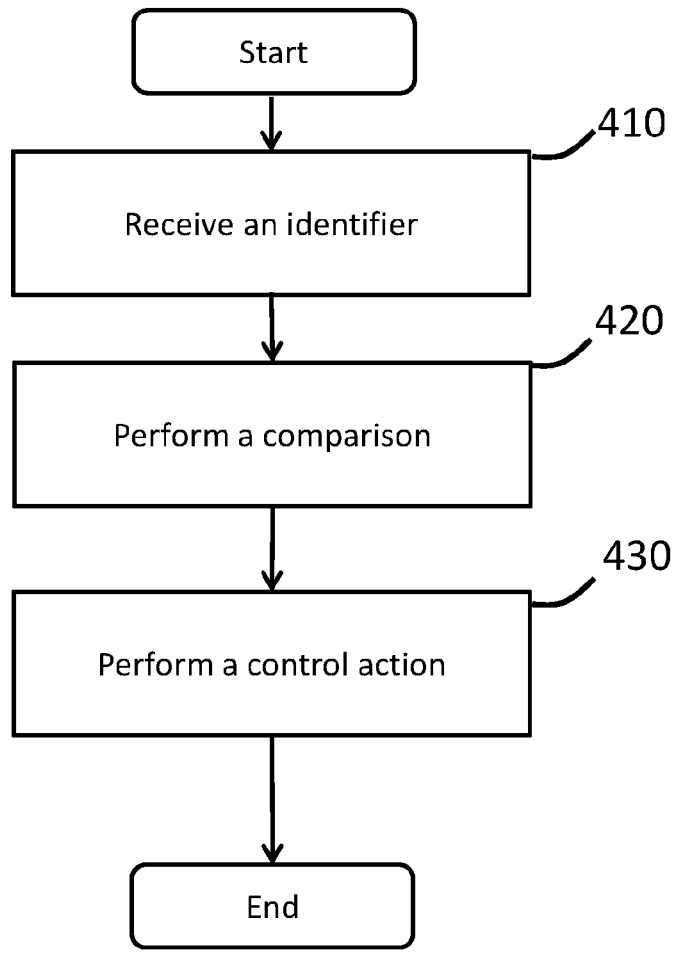
FIG. 3 is a schematic flow diagram of another method to be performed by a control unit according to various implementations of the disclosure.

FIG. 3 shows a flowchart of an example method of operating an electronic aerosol provision system 100 such as shown in FIG. 1 (or the control unit 101 thereof), whereby an identifier received from a cartridge is compared with a set of stored identifiers in memory 180. Note that the method of FIG. 3 may occur independently of, in parallel with, or subsequently to the method of FIG. 2.

In 410, the control unit 101 receives an identifier from a cartridge 102 or other consumable (disposable) component which is typically being engaged with (received into) the control unit 101 to form an electronic aerosol provision system. In some implementations, the identifier may be received over (or by) a connection interface 105 which is provided between the cartridge 102 and the control unit 101.

In 420, the control unit 101 performs a comparison of the received identifier against the set of stored identifiers held in memory. The control unit, for example, the processor 185 of the control unit, is configured to compare the received identifier with each identifier of the set of stored identifiers to determine whether the received identifier matches one of the stored identifiers. Finding a match may indicate, for example, that the cartridge can be considered genuine, and hence properly compatible with the control unit 101.

In 430, the control unit 101 performs some control action which is dependent upon the result of the comparison of 420. In some cases, the control action may be dependent upon whether the comparison finds any match for the received identifier in the set of stored identifiers—which may confirm that the cartridge 102 is genuine, as suggested above. In other cases, the control action may be dependent upon which particular identifier in the set of stored identifiers is matched by the received identifier. For example, matching different stored identifiers may correspond to applying a different resistance to draw or different heating profiles to operation of the vaporizer. In some cases, there may be multiple control actions dependent upon the result of matching an identifier. Furthermore, there may be a default control action (or actions) if no match is found between the received identifier and the set of stored identifiers. For example, the default control action may include disabling (or not enabling) the heater by preventing the supply of power to the heater.

Figure 4:
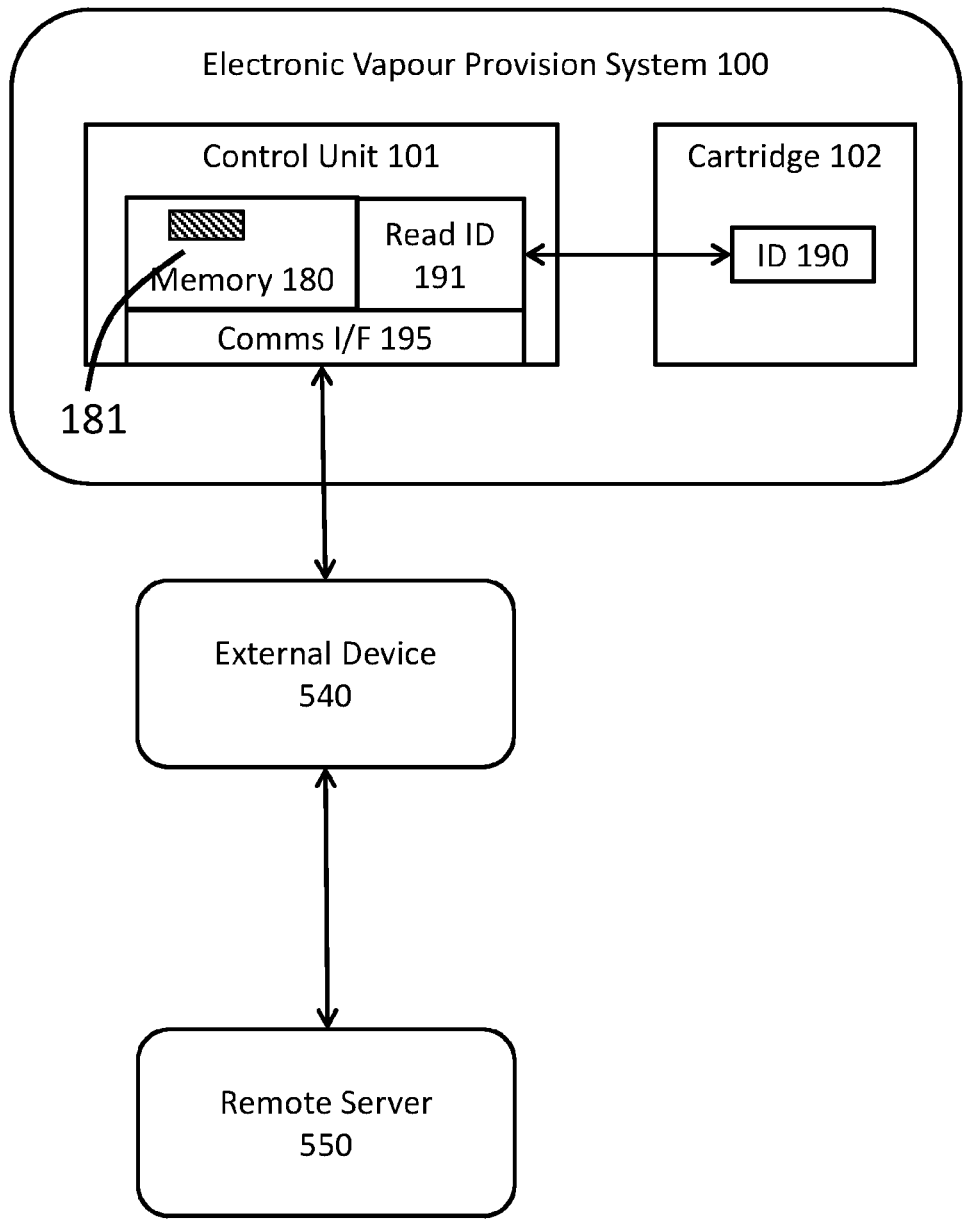
FIG. 4 is a schematic diagram showing communications between different systems and devices according to various implementations of the disclosure.

FIG. 4 is a schematic diagram showing communications between different systems and devices according to various implementations of the disclosure. In particular, FIG. 4 illustrates an electronic vapor provision system 100 (electronic aerosol provision system), such as shown in FIG. 1, comprising a re-usable component, such as control unit 101, and a replaceable component, such as cartridge 102. The cartridge 102 includes a consumable component (not shown), such as an e-liquid or a tobacco plant derivative (such as dried leaves). The consumable component acts as a vapor or aerosol precursor, and when heated generates a vapor/aerosol for inhalation by a user. The control unit 101 typically includes a rechargeable battery (not shown) for providing power to the heater used to generate the vapor/aerosol from the precursor material.

The cartridge 102 further includes an identifier (ID) component 190, which may be provided in various different ways as discussed above—for example as a bar code marking for optical reading, as an electronic memory, etc. The control unit 101 includes an ID reader 191 which is able to receive (e.g. read or access) the ID from the ID component 190, typically when the cartridge 102 is coupled to (engaged with or received into) the control unit 101, or perhaps when the cartridge is otherwise brought close to the control unit. It will be appreciated that the nature of the ID reader 191, and the specifics of how the ID is received from the cartridge 102, depend on (and correspond to) the implementation of the ID component 190. For example, if the ID component 190 comprises a bar code, then the ID reader 191 typically comprises some form of optical reader; if the ID component 190 comprises electronic memory, such as a ROM, then ID reader 191 may be implemented as an electronic read facility, and may be incorporated (for example) into processor 185.

In addition to ID reader 191, the control unit 101 includes a communications interface 195 and a memory 180. The memory is used, inter alia, to hold a set of stored identifiers 181. The memory may also hold (or support access to) various control (operational) actions that are associated with the identifiers. For example, the control actions may comprise heating profiles (how long a heater should be operated and at what power levels), airflow profiles (selection of a particular resistance to draw by adjusting the airflow modifier, as described below), whether to allow operation of the device for vapor generation, display of messages to a user, and so on. The control unit 101 is configured to perform one or more control actions dependent upon the match (or otherwise) between the stored identifiers and the received identifier. Note that multiple stored identifiers may match to a given control action. For example, one heating profile may be suited for a first set of batch numbers for the cartridge 102, another heating profile may be suited for a second set of batch numbers for the cartridge.

The list of identifiers 181 is maintained by communications between the electronic vapor provision system 100 and a remote server 550. FIG. 4 shows an external device 540, such as a smartphone and app, mediating these communications (which typically occur over the Internet), however, in some cases the electronic vapor provision system 100 and the remote server 550 may be able to communicate directly with one another, so that external device 540 may be omitted. The communications interface 195 to support such direct or indirect communications may be implemented in various ways, for example, using a USB link (which may also be used for recharging the battery in the control unit 101) or by using a wireless connection such as Bluetooth to the external device. In some devices, the communication interface 195 may support multiple forms of connectivity.

The control unit 101 may receive updates for the stored identifier listing 181 from the remote server 550 at various times, for example, the control unit may contact the remote server 550 when network connectivity is established (and optionally when such contact has not been performed for a given time period). The control unit 101 may also contact the remote server if the control unit 101 receives an identifier from the cartridge 102 that it does not recognize, i.e. that does not match anything in the list of stored identifiers 181. The remote server may then be able to provide an up-to-date match for this identifier (if available).

In some systems, the control unit may be configured to always request information from the remote server 550 for an identifier which is newly received from a cartridge 102. In this case, the control unit may not include memory 180, which can reduce costs. On the other hand, having the stored set of identifiers 181 in memory 180 allows the matching of the received identifier to be performed more quickly, without any communication delays (and without requiring any network connectivity).

As described herein, a control device for an electronic aerosol provision system is provided. The control device is configured to receive a replaceable component to form an electronic aerosol provision system. The control device includes a communication interface for performing communications external to the electronic aerosol provision system; a memory configured to hold a set of stored identifiers; and a control system. The control system is configured to: receive control information from a remote server via the communication interface; update the set of stored identifiers based on the control information received from the remote server; receive an identifier from a replaceable component coupled to the control device; make a comparison of the received identifier against the set of stored identifiers; and perform a control action for the electronic aerosol provision system dependent upon the result of said comparison.

In some implementations the replaceable component contains a consumable material, such as an aerosol precursor material. The control action may be targeted at the particular consumable (aerosol precursor) material contained in the replaceable component, for example, the control action may specify how best to generate an aerosol from the aerosol precursor material. In other implementations, the replaceable component might not contain an aerosol precursor material. For example, the control unit might initially be supplied with a first, non-refillable (by the user), replaceable component. This initial replaceable component may then be removed and replaced by a second replaceable component, which is empty of a consumable material when received into the control unit, but may be subsequently be (re)filled by the user with an aerosol precursor material for use as an electronic aerosol provision system. In some implementations, the replaceable component may be an element which is attachable to the control unit and is intended to be replaced periodically. For example, it is known in some THP devices for a tubular sleeve to be inserted into a heating chamber of the control unit, with rod-like consumables then being inserted into the sleeve for heating. Each pack of 20 consumables may be provided with such a sleeve. For such an arrangement, it may be easier (and more cost-effective) to provide the identifier on each sleeve (as a replaceable component), rather than on every rod-like consumable.

The identifier received from the replaceable component may comprise (or consist of) information specific to the replaceable component, for example, one or more of a unique serial number, a model number, a date of manufacture, a use-by date, an authentication code, information about the consumable material in the replaceable component such as batch number, blend or flavor, one or more operating parameters to apply in the control device (control unit), such as a heating profile, information to provide to a consumer, such as a description of the consumable material in the replaceable component.

A further possibility is that the identifier is a reference that can be sent to a remote server to obtain some or all of the information specific to the replaceable component. Combinations of these implementations are also possible, in which the identifier includes some information specific to the replaceable component and also provides a reference to access other such information from the remote server.

The control system of the control device, which may be implemented for example by the control circuitry 175 shown in FIG. 1, compares the received identifier against the set of stored identifiers. In some cases this comparison may look for a direct match of the received identifier against a stored identifier. In other cases, a different form of comparison may be utilized. For example, the stored identifiers may be configured in pairs, each pair defining a range of model numbers. In this case, the comparison determines whether the received identifier falls within the range of model numbers defined by one or more pairs of model numbers (which can then be regarded as a match).

If the received identifier comprises multiple pieces of information, for example, multiple components, then two or more components could potentially be compared separately against the information of the stored identifiers (and more particularly, against the relevant components thereof). For example, a given identifier may comprise both a flavor of the material in the replaceable component and also operating parameters for use in heating this material.

The control device performs at least one control action for the electronic aerosol provision system dependent upon the result of comparing the received identifier against the stored identified. For example, if a match is found, the control device might perform one or more actions specific to the matched identifier, such as heating using a heating profile specific to the matched identifier, whereas if no match is found, the control device might utilize a default heating profile. In another example, if a match is found, the control device might allow operation of the electronic aerosol provision system to generate vapor, but if no match is found, the control device may provide a reduced level functionality for the electronic aerosol provision system. In one such case, if there is no match, operation is disabled (or not enable), such as because it cannot be confirmed that the replaceable component is compatible with the control device.

In some cases, the control action(s) may depend upon a binary outcome of the comparison (whether there is a match, yes or no), in other cases, some or all of the control(s) may depend on the particular match that is achieved. In the latter situation, different control actions may be associated with different stored identifiers (or groups or subsets of stored identifiers). These control actions may also be stored in memory 180, or may be stored elsewhere, but referenced from memory 180, thereby allowing the electronic aerosol provision system to perform one or more control action specific (and appropriate) to the particular matched identifier(s). In some cases multiple actions may be performed in response to a match (or matching of different components), for example, a heating profile may be selected, and information provided to the user on display 173. The action(s) performed may depend on which component(s) of an identifier find a matched in the stored identifiers.

The control device interacts with the remote server to update the set of stored identifiers. For example, the control device may use control information received from the remote server to add, delete, or modify one or more identifiers of the set of stored identifiers. In this way, the control device can be prepared, for example, for use with new types of replaceable component that may not have been available when the control device was originally sold. The control information may likewise be utilized to update the stored actions associated with the set of stored identifiers, for example, by modifying the control actions themselves, and/or by changing the association between different identifiers and different control actions.

In some cases the remote server may push updated control information out to electronic aerosol provision devices, in other cases, the control system may send a request for updated control information from the remote server. For example, the control system may send such a request on a weekly basis, or perhaps whenever it establishes network connectivity (or some other set of criteria). The control system may also send a request for updated control information from the remote server in response to a received identifier not matching one of the stored identifiers. The control system may receive updated control information from the remote server in response to such a request, which can then be used to assess the received identifier as discussed above, i.e. by making a comparison of the received identifier against the updated set of stored identifiers, and then performing a control action for the electronic aerosol provision system dependent upon the result of this comparison.

In some cases, the electronic aerosol provision system is used with a replaceable component that forms a tobacco heated product (THP). In some cases, the aerosol precursor material in a consumable THP product may be more susceptible to variation, being directly derived from a natural product. Accordingly, the identifier in the consumable may be used to, for example, to indicate a particular blend of tobacco(s) or a particular batch of the consumable, and a heating profile (and/or resistance to draw) that is chosen for such blend or batch.

While it has generally been described above that the container 120 is formed of a plastics material and includes a portion of solid aerosol precursor material therein, in other implementations the container 120 may be formed of a paper or card material. In some implementations, the paper or card material is wrapped around the outer surface of aerosol forming material formed substantially into a rod-shape. Such a container 120 may be formed in a similar manner to combustible cigarettes, and may also include an integrated mouthpiece (e.g., a filter) at one end thereof. The general approach of heating the container described above still applies, namely the container is heated, but not burnt, to generate an inhalable aerosol. With these containers, the identifiers may be provided in any suitable manner as described above, e.g., they may be optically printed on the surface of the container.

Returning to FIG. 3, in some cases the control action 430 may involve the control device 101 outputting information relating to a received cartridge by using display 173 (or some other output device as appropriate). In some implementations, such a control action may be stored in memory 180 and accessed and performed in response to the received identifier matching a stored identifier associated with providing this output. In other implementations, the control unit 101 may transmit the received identifier to the remote server 550 (possibly via some intermediary device 540 such as shown in FIG. 4), and the remote server then returns to the e-cigarette 100 the relevant control action (or information identifying such control action) to perform for the receiving identifier—such as outputting information relating to the cartridge from which the received identifier was obtained.

As described above, the display may be implemented in various ways, for example, using one or more light emitting diodes (LEDs) (potentially multi-colored) and/or as a (small) liquid crystal display (LCD) screen. In the latter case, the control unit 101 may utilize the display 173 to provide feedback to a user by displaying a verbal message comprising one or more words, etc.; in the former case, the control unit may illuminate a particular LED (or pattern of LEDs) of display 173 to provide feedback to a user. In some cases, a color and/or temporal pattern may also be applied to the LED light(s), such as flashing on and off, changing color, etc., to help convey the desired information to the user. In addition, the display 173 may be supplemented by audio and/or haptic feedback to a user, and/or by also providing output information to an external device 540 connected to the e-cigarette 100 through the communications interface 195. As discussed above, the external device 540 could be a smartphone or personal computing device for example; such external devices often provide a more extensive and powerful user interface (for both output and user input) than may be available on an electronic aerosol provision device 100.

The following are (non-limiting) examples of messages that might be provided to the user in such a manner:
- a confirmation, such as a green light or OK message, that a newly inserted cartridge has been recognized and is available to use (this might typically be provided when the received identifier has successfully matched a stored identifier).
- a warning indication, such as a red light or error message, that a newly inserted cartridge has not been recognized and is therefore not available to use (this might typically be provided when the received identifier has not matched any stored identifier).
- a warning indication that a newly inserted cartridge has passed its use-by (expiry) date (this might typically be determined from a component of the received identifier, or by using the received identifier to access such information either locally within memory 180 and/or remotely from server 550).
- information about the consumable material in the received cartridge, such as the name of a material or blend, manufacturer, grade, variety, etc. (again this might typically be determined from a component of the received identifier, and/or by using the received identifier to access such information either locally within memory 180 and/or remotely from server 550).

In some circumstances, the display 173 may be used not only to provide information to the user about a newly received cartridge, but also to collect user input, such as control information for use with the cartridge. For example, having identified the cartridge type (such as the material and flavor) to the user, the display may request from the user a power level setting for operating this cartridge (whereby operating at a higher level may produce more vapor for each inhalation, but will consume the material more quickly). The user can then respond as appropriate to provide the desired control setting.

In some implementations, the control action 430 of FIG. 3 may be used to control or adjust the resistance to draw (RTD) of the electronic aerosol provision system 100. The RTD, which is sometimes referred to as the pressure drop, is the perceived resistance a user feels when the user inhales on the electronic aerosol provision device (or a conventional cigarette), and affects the airflow through the e-cigarette. The RTD is generally a function of the cross-sectional area of the air flow channel, the length of an airflow channel, and the characteristics of the intake air (i.e., ambient air) and the aerosol produced.

RTD is one of the parameters that influence user experience of an e-cigarette (and also a conventional cigarette). Users often expect a given device to provide a consistent level of RTD, whereby deviations from this consistent level might be seen as a variation in quality, and/or detract from the user experience.

The RTD may increase as the cross-sectional area of an airflow channel is reduced. In many practical situations, the overall RTD of an electronic aerosol provision device is primarily determined by the size of the narrowest portion of the airflow channel. In other words, the dominant contributor to RTD is usually this narrowest portion of the airflow channel. Thus controlling this narrowest portion (smallest cross-sectional area) of the airflow channel in turn allows the RTD to be controlled.

The airflow modifier 200 shown in electronic aerosol provision system 100 of FIG. 1 provides a facility to alter or adjust the RTD of the electronic aerosol provision system 100. Altering the RTD may, for example, change the volume of air passing through the container 120 during a user inhalation, which may in turn modify the concentration and/or composition of the vapor or aerosol inhaled by the user.

Figure 5A:
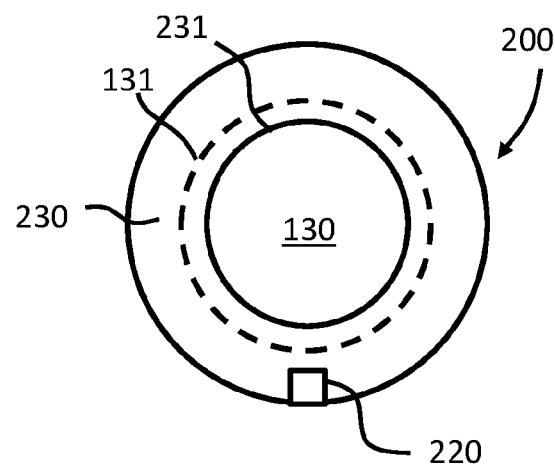
FIGS. 5A and 5B are schematic diagrams showing different mechanisms for controlling the resistance to draw according to various implementations of the disclosure.

FIG. 5A shows a schematic cross-sectional view of the primary airflow path (airflow channel 130) including one example of airflow modifier 200. The airflow modifier 200 is operable to modify (alter, change, or adjust etc.) the airflow pathway such that the resistance to draw through this portion of the airflow channel can be changed in a controlled manner, for example by control circuitry 175, e.g. processor 185.

The airflow modifier 200 of FIG. 5A surrounds the airflow channel 130 and comprises a movable iris or diaphragm 230 and surrounded by an actuator 220. The iris comprises a ring having an inner diameter which can be adjusted by the actuator. The airflow modifier 200 is inserted into the air channel 130 at a break in the sidewall 131 (indicated schematically in FIG. 5A by having a dashed line to represent the sidewall 131). In other words, a first portion of the airflow sidewall 131 is located upstream of the iris 230 and a second portion of the airflow sidewall is located downstream of the iris 230. The airflow modifier then acts as a join or coupling between these first and second portions of the airflow sidewall 131 to maintain an airtight seal for the airflow channel 130. In an alternative configuration, the whole of the iris 230 may be fitted internally to the airflow channel 130 or positioned at an end (inlet or outlet) of the airflow channel 130.

The iris 230 may comprise several portions configured to move, e.g. rotate, relative to each other such that a substantially circular profile with an adjustable diameter is created by an inner edge 231 formed from these portions (analogous, for example, to the operation of a camera shutter or aperture control). The actuator 220 receives power from the battery 177 to move the iris 230 in this manner under the control of the control circuitry 175. The actuator 220 is therefore able to adjust the iris 230 between different positions such that the inner edge 231 provides a variable cross-sectional area for this portion of the airflow channel 130. Thus by decreasing the diameter of the aperture formed by the iris 230, the cross-sectional area of the airflow path is reduced and the flow of air through the channel 130 is more restricted. In contrast, by increasing the diameter of the aperture formed by the iris 230, the cross-sectional area of this portion of the airflow path is enlarged and the flow of air through channel 130 is less restricted. This in turn allows the resistance to draw of the airflow channel to be adjusted, especially if the cross-sectional area through the airflow modifier is generally smaller than the cross-sectional area through the remainder of the airflow channel (since in this case the airflow modifier will make a significant, potentially dominant, contribution to the resistance to draw of the overall airflow channel 130).

The actuator 220 receives electrical power from the battery 177 and may convert this into motion of the iris 230 according to any appropriate method. For example, the actuator 220 may generate motion using the piezo-electric effect. Alternatively, the actuator may generate motion using an electromagnetic field resulting from an electric current (as for a conventional electric motor). Alternatively, the actuator 220 may generate motion by thermal expansion resulting from heating by an electric current. Other techniques for driving motion of the actuator 220 may be apparent to the skilled person.

Although the actuator 220 and the iris 230 are shown in FIG. 5A as separate components, in some implementations, they may be provided as an integral device, in which movement of the actuator itself changes the cross-sectional area of the airflow channel 130. A further possibility is that the actuator 220 and the iris 230 may be separated from one another—for example, if the actuator uses an electro-magnetic field and/or inductive heating to drive the iris 230. In this case, the actuator may potentially be located outside the airflow channel 130 (and sidewall 131), while only the iris 230 is located inside the airflow channel (separated from the actuator 220 by the sidewall 131. One advantage of locating components outside the airflow channel 130 (and outside airflow sidewall 131) is that it avoids the risk that such a component may contaminate the airflow through the electronic aerosol provision system, this airflow subsequently being inhaled by a user.

Figure 5B:
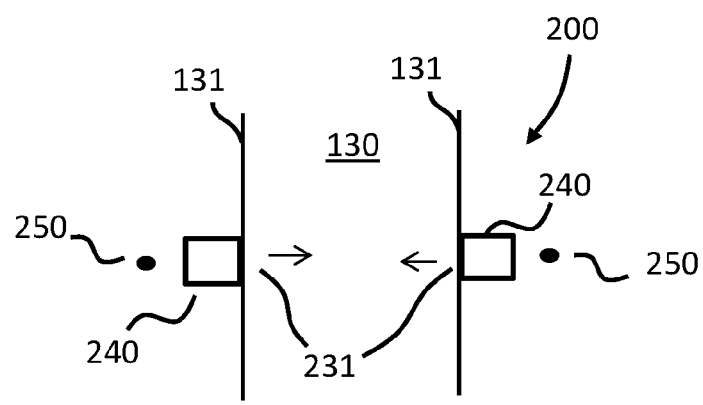

FIG. 5B shows a schematic cross-sectional diagram of another example of airflow modifier 200, such as may be used in the electronic aerosol provision device 100 of FIG. 1 to control resistance to draw. In FIG. 5B, the airflow modifier 200 is situated adjacent to airflow pathway 130 and comprises a pair of permanent magnetic segments 240 (such as diamagnets) attached to the outside of the airflow sidewall 131. The airflow modifier further includes an electrically conductive coil or wire loop 250 (having a suitable support structure, not shown in FIG. 5B). The control circuitry 175 provides power from the battery 177 to the coil 250 to generate a magnetic field that interacts with magnetic segments 240 to push the magnetic segments towards the center of the airflow channel 130. The sidewall 131 is sufficiently flexible to accommodate such movement and this in turn reduces the cross-sectional area of the airflow path, and hence increases the resistance to draw of this portion of the airflow path. Furthermore, the amount of deflection of sidewall 131 can be controlled by varying the strength of the current through coil 250, which in turn controls the strength of the electromagnetic field generated to repel the magnetic segments 240.

It will be appreciated that although FIG. 5B shows a pair of magnetic segments 240, a different number of segments may be used. For example, a single magnetic segment 240 might be used to push the airflow channel against a fixed structure, which would then compress the airflow channel and so reduce its cross-sectional area. Alternatively, there may be more than two magnetic segments azimuthally arranged around the circumference of the airflow channel 130 (in a plane substantially perpendicular to the airflow direction). In addition, while the magnetic segments 240 are shown in FIG. 5B as located on the outside of the airflow sidewall 131, in some cases they may be attached to the inside of the airflow sidewall 131, or potentially join two portions of the airflow sidewall (analogous to the positioning of FIG. 5A). Furthermore, although the implementation of FIG. 5B uses an electro-magnetic force to move the airflow sidewalls 131 to increase the RTD, other implementations may use different methods of moving the airflow sidewall 131, for example, based on the piezo-electric effect or thermal expansion as described above in relation to FIG. 5A.

It will be appreciated that while FIGS. 5A and 5B provide examples of the airflow modifier 200, the skilled person will be aware of many other possible implementations. Furthermore, although FIG. 1 shows an electronic aerosol provision system 100 having a single airflow modifier 200 positioned partway along the airflow channel 130 in the control unit 101, in other implementations the airflow modifier 200 may be positioned at an air inlet or air outlet for the airflow channel, and/or the airflow modifier may be located in the cartridge 102. For example, the airflow modifier 200 may be provided within the cartridge 102 upstream or downstream of the container 120; one possibility for the latter approach would be to incorporate the airflow modifier 200 into the mouthpiece 118. In general, if an airflow modifier 200 is located within the cartridge, interface 105 may comprise additional electrical connections (wired or otherwise) to enable the control circuitry 175 to control (and power) the airflow modifier 200.

Moreover, an electronic aerosol provision system 100 may be provided with two or more airflow modifiers 200, which may be co-located or spread along the airflow channel 130, and potentially split between the control unit 101 and the cartridge 102. Furthermore, if multiple airflow modifiers 200 are present, they may all be of the same type, or there may be two or more different types. For example, an electronic aerosol provision system 100 might be provided with a first airflow modifier 200 such as shown in FIG. 5A and a second airflow modifier such as shown in FIG. 5B.

As described above, resistance-to-draw (RTD) measures the pressure drop required to draw a given rate of airflow through a structure, such as an electronic aerosol provision system 100. RTD therefore reflects the suction effort of a user to inhale airflow at a given rate through the device. By altering the diameter of the iris 230 in a portion of the airflow channel 130 to change the cross-sectional area of a corresponding portion of the primary airflow path, the RTD of the device is changed.

The airflow modifier 200 may be controlled by the control device, such as by using control circuitry 175 in accordance with programming instructions stored, for example, in memory 180. These instructions may be associated with (or accessed using) the stored identifiers 181, as described above. The programming instructions allow the control circuitry 175 to alter the RTD of the e-cigarette by controlling the RTD of the airflow modifier 200. Accordingly, controlling the RTD may represent a further control action according to operation 430 of FIG. 3, which involves receiving an identifier from the cartridge 102 and performing a comparison of the received identifier with the set of stored identifiers in the memory 180.

As one example of this operation, let the RTD of the control unit be $R_K + R_{AM}$, where $R_K$ is a constant, and $R_{AM}$ is the RTD of the airflow modifier 200 (which is assumed here to be located in the control unit). The stored identifier received from the cartridge 102 may indicate that the RTD of the cartridge 102 is $R_C$ (this may be directly provided by the received identifier itself, or the received identifier may allow $R_C$ to be accessed, whether from memory 180 or from remote server 550). The control unit may then set $R_{AM}$ such that $R_{AM} = R_T - R_C - R_K$, where $R_T$ is a desired total RTD for the complete electronic aerosol provision system 100 (since RTD is additive in series, analogous to conventional electrical resistance). It will appreciated that in this approach, the RTD of the airflow modifier 200 is adjusted to compensate for different values of RTD for different cartridges 102, thereby providing the user with a consistent experience across a range of different cartridges. This facility is especially helpful in the context of THPs, where difference types of THP consumable material (e.g. powder, dried leaves, etc) may have a different RTD, and even different cartridges (or different batches of cartridges) of THP consumable material may have a different RTD due to natural product variation, different blends, etc.

Although the electrical (electronic) control of the airflow modifier 200 as described above is dependent upon the received identifier, in other implementations the airflow modifier 200 may additionally or alternatively be dependent upon other factors. For example, in some implementations, the user may be provided with a control setting to adjust the RTD, such as to reflect user preference. The control facility 175 then adjusts the RTD of the airflow modifier 200 to reflect the user setting. As another example, RTD controls airflow rate through the device (for a given pressure drop, i.e. for a given strength of inhalation). Note that the airflow rate also impacts the rate of aerosol or vapor drawn from the device, and hence the heating power required (since a high airflow rate tends to cool the heater more). The control unit 101 in some devices might therefore raise the RTD to reduce the power drain on the battery (since a higher RTD will reduce the airflow rate and hence the heating requirement). Such a reduction in power drain might be desirable if the battery charge is nearly depleted, firstly to conserve battery lifetime, and/or secondly because the battery output voltage may have declined (relative to a fully charged battery), so there is less power available from the battery.

It will therefore be understood that the ability to control RTD via airflow modifier 200 represents a separate control parameter for the operation of the electronic aerosol system 100, which can be used in conjunction with other parameters, such as a heating power, heating duration, etc., to provide desired operational characteristics for the device. For example, if the control circuitry 175 is able to adjust both RTD and heater power levels, these parameters may be controlled in complementary fashion. Thus heating of the material within a container 120 may be dependent on factors such as the material composition, the heater power level and the airflow through container 120. For a given material in a container 120, the heater power level and the RTD (and hence airflow) may be controlled to provide a desired heating of the material, whereby an increased airflow (lower RTD) through the material may result in a lowering of the temperature of the material, while a reduced airflow (higher RTD) may result in an increase of the material temperature. This additional control provided by the airflow modifier may be used to help avoid over-heating or under-heating of the material. Note that such control may be performed dynamically, within the duration of a single puff, especially in conjunction with some form of feedback loop that estimates the current temperature of the material, e.g. as obtained from a temperature sensor, or estimated from the power draw from the battery. Accordingly, the provision of the airflow modifier 200 helps to support a consistent, reliable, and configurable user experience of the electronic aerosol provision device 100.

As another example, a higher RTD will produce a lower airflow rate, thereby typically increasing the concentration in the airflow of the aerosol generated from the aerosol precursor material in container 120 and as inhaled by a user. In contrast, a lower RTD will increase the flow rate, potentially leading to a lower concentration of aerosol in the inhaled airflow. It will be appreciated that different concentrations of aerosol or vapor may suit different users and/or different consumable materials. Likewise, different users may produce different levels of pressure drop, depending on their strength of inhalation, and controlling the RTD can be used to generate a more predictable and consistent product experience in terms of airflow rate and vapor concentration across these different inhalation strengths.

It should also be appreciated that in some implementations, different aerosol precursor materials may deliver different experiences to the user when inhaled under different RTDs. For example, the manner in which flavor is delivered to a user may be dependent upon the RTD. Therefore, in some implementations, the aerosol provision system may be configured to alter the RTD, not necessarily to provide a consistent RTD to a user, but instead to provide a suitable RTD depending upon the aerosol precursor material and/or replaceable component that is used.

Accordingly, as described herein, a control device for an electronic aerosol provision system is configured to receive a replaceable component comprising an aerosol precursor material to form an electronic aerosol provision system. The control device is further configured to receive an identifier from a replaceable component received by the control device; and to modify the resistance to draw (RTD) of an airflow path through the electronic aerosol provision system dependent upon the received identifier.

Such modification of the RTD can be useful to compensate for variation in the RTD of the replaceable component, especially in situations where there may be a range of RTD for such components (for example, due to natural variability in THP products). For example, the control device may be configured to modify the RTD of an airflow path through the electronic aerosol provision device dependent upon the received identifier to provide a substantially consistent RTD for the electronic aerosol provision system for various different received replaceable components. Control of the RTD can also be used, for example, to provide an additional control parameter relevant to the aerosol generation by heating.

In general terms the RTD can be increased by lengthening the overall airflow path, and/or by reducing the cross-section of the airflow path (most effectively at the narrowest portion of the airflow). Although the former approach (lengthening the overall airflow path) may be implemented in some systems, modifying the resistance to draw by altering the cross-sectional area of the airflow path usually gives the greatest level of control over the RTD.

As described herein, one or more airflow modifiers may be provided within the electronic aerosol provision system (within the control device and/or within the replaceable component) to modify the cross-sectional area of the airflow path, for example, by using a diaphragm that can be widened or narrowed accordingly. Such an airflow modifier may be electrically operated using power from a re-chargeable battery of the control device, with the diaphragm being actuated, for example, using an electro-magnetic field due to current flow, thermal expansion due to current flow, and/or the piezo-electric effect.

As also described herein, a control device for an electronic aerosol provision system is configured to receive a replaceable component comprising an aerosol precursor material to form an electronic aerosol provision system. The control device is further configured to: receive an identifier from a replaceable component received by the control device; and to provide output to a user based on the received identifier. In some cases, this output may be provided using a display of the electronic aerosol provision system (such as LED lighting or an LCD display panel). Such a display is typically located in the control device, but may potentially be located, at least in part, in the replaceable component. In some implementations, the output may be transmitted from the control device to another (local) system for display, for example, to a user smartphone, tablet, etc., by using any appropriate communications technology, such as USB, Bluetooth, NFC, and so on.

The output may be dependent upon an authorization of the received identifier; for example a red light might be illuminated to indicate a replaceable component has been attached which is not authorized (e.g. the received identifier does not match a stored identifier), while a green light could indicate an authorized replaceable component. As another example, the output may provide information about a consumable material in the replaceable component from which the identifier was received. This may in turn prompt the user to enter one or more control settings appropriate to how the user wishes to operate the electronic aerosol control system in conjunction with such consumable material.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc., other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. A control device for an electronic aerosol provision system, the control device being configured to receive a replaceable component to form an electronic aerosol provision system, the control device being configured to:
   receive an identifier from the replaceable component received by the control device; and
   modify one or more characteristics of an airflow path through the electronic aerosol provision system dependent upon the received identifier;

wherein the one or more characteristics of the airflow path through the electronic aerosol provision system comprise resistance to draw.

2. The control device of claim 1, wherein the control device is configured to modify the resistance to draw of the airflow path through the electronic aerosol provision system dependent upon the received identifier to provide a substantially consistent resistance to draw for the electronic aerosol provision system for different received replaceable components.

3. The control device of claim 1, wherein the output provides information about a consumable material in the replaceable component from which the identifier was received.

4. The control device of claim 1, wherein the control device further includes a communication interface for interacting with a remote server either directly or indirectly via a smartphone.

5. An electronic aerosol provision system comprising the control device of claim 1.

6. The control device of claim 1, wherein the control device is configured to modify the resistance to draw by modifying a cross-sectional area of the airflow path in at least one location.

7. The control device of claim 6, wherein the control device is configured to modify the resistance to draw at an inlet or an outlet of the airflow path.

8. The control device of claim 1, wherein an airflow modifier is provided to modify at least one of a cross-sectional area or a length of the airflow path.

9. The control device of claim 8, wherein the airflow modifier comprises a diaphragm that can be widened or narrowed to modify the cross-sectional area of the airflow path.

10. The control device of claim 8, wherein the airflow modifier is either:
located in the control device; or
located in the replaceable component.

11. The control device of claim 8, wherein the airflow modifier is electrically operated to modify at least one of the cross-sectional area or the length of the airflow path.

12. The control device of claim 11, wherein the electrical operation of the airflow modifier includes generating a magnetic field to modify the cross-sectional area of the airflow path.

13. The control device of claim 11, wherein the electrical operation of the airflow modifier utilizes thermal expansion to modify the cross-sectional area of the airflow path.

14. A control device for an electronic aerosol provision system, the control device being configured to receive a replaceable component to form an electronic aerosol provision system, the control device being configured to:
receive an identifier from the replaceable component received by the control device; and
provide output to a user based on the received identifier,
wherein the output is provided on a display of the electronic aerosol provision system, and
wherein in response to identifying the replaceable component, the display is configured to collect user input comprising control information for use with the replaceable component.

15. The control device of claim 14, wherein the control device is configured to transmit the output for display on an external system.

16. The control device of claim 14, wherein the output is dependent upon an authorization of the received identifier.

17. The control device of claim 14, wherein the output provides information about a consumable material in the replaceable component from which the identifier was received.

18. A method of operating a control device for an electronic aerosol provision system, the method comprising:
receiving a replaceable component to form an electronic aerosol provision system;
receiving an identifier from the replaceable component; and
in response to the received identifier:
modifying one or more airflow characteristics of an airflow path through the electronic aerosol provision system dependent upon the received identifier, wherein modifying one or more airflow characteristics of the airflow path through the electronic aerosol provision system comprises modifying a resistance to draw of the airflow path.

19. A method of operating a control device for an electronic aerosol provision system, the method comprising:
receiving a replaceable component to form an electronic aerosol provision system;
receiving an identifier from the replaceable component; and
in response to the received identifier:
providing output to a user based on the received identifier using a display of the electronic aerosol provision system,
wherein in response to identifying the replaceable component, the display is configured to collect user input comprising control information for use with the replaceable component.

* * * * *